US00PP09347P

United States Patent [19]

Zerr

[11] Patent Number: Plant 9,347

[45] Date of Patent: Oct. 31, 1995

[54] POINSETTIA PLANT NAMED 'FISBON'

[75] Inventor: Katharina Zerr, Simmern, Germany

[73] Assignee: Florfis AG, Binningen, Switzerland

[21] Appl. No.: 327,929

[22] Filed: Oct. 24, 1994

[30] Foreign Application Priority Data

Dec. 29, 1993 [DE] Germany ..... EUP 150

[51] Int. Cl.[6] ..... A01H 5/00

[52] U.S. Cl. ..... Plt./86.4

[58] Field of Search ..... Plt./86.4

[56] References Cited

U.S. PATENT DOCUMENTS

P.P. 5,492 6/1985 Gutbier ..... Plt./86.4

P.P. 8,259 6/1993 Jacobsen ..... Plt./86.4

*Primary Examiner*—James R. Feyrer

*Attorney, Agent, or Firm*—Foley & Lardner

[57] ABSTRACT

A distinct cultivar of poinsettia plant named Fisbon, characterized by the combined traits of orange-red bract color, medium and well branched plant habit, medium green foliage, no tendency to develop a bluish tint, and its good performance in early culture under high temperatures.

1 Drawing Sheet

Fisbon is a product of a mutation induction program carried out by the invention in Hillscheid, Germany in 1991. The primary objective of the induction program was to expand the bract color ranges of Peterstar, disclosed in U.S. Plant Pat. No. 8,259 and characterized by its bright red bract color, medium green foliage, comparatively compact plant habit, medium early response in autumn, and good branching ability.

The irradiation program resulting in the new cultivar comprised exposing rooted cuttings of the parent cultivar to an X-ray source of 30 Gy in Ahrensburg, Germany under the supervision of the inventor Katharina Zerr in 1991. The irradiated plants were grown out in a greenhouse in Hillscheid, Germany and were asexually propagated by taking cuttings. These cuttings were grown outdoors near Galdar, Gran Canaria, Spain, under the supervision of the inventor. Parts of plants showing mutation were cut from the remainder of the plants by the inventor and planted as cuttings. The plants grown from these cuttings were identified by number and selections were made by the inventor in autumn 1991.

The new cultivar evolved from a branch of an irradiated plant having speckles and marbled red bract color. The plant was grown out and propagated several times by cuttings by the inventor. Selections were made of plants with uniform orange-red flower color. One such selection, identified as plant No. 263, comprised the new cultivar.

The new cultivar was thereafter propagated several times in Hillscheid, Germany in order to eliminate chimeras and to obtain a plant with stable and uniform characteristics.

The following traits have been repeatedly observed and are determined to be basic characteristics of Fisbon which in combination distinguish this poinsettia as a new and distinct cultivar:

1. Orange-red flower color.
2. No tendency to develop a bluish tint.
3. Medium tall and well branched plant habit.
4. Medium green foliage.
5. Good performance in early culture under high temperatures.

Fisbon has not been observed under all possible environmental conditions. The phenotype may vary significantly with variations in environment such as temperature, light intensity, and daylength without, however, any variance in genotype. The following observations, measurements and comparisons describe plants grown in Hillscheid, Germany, under greenhouse conditions which approximate those generally used in commercial practice.

Of the many commercial cultivars known to the inventor, the most similar in comparison to Fisbon is the parent cultivar Peterstar. In comparison to Peterstar, the bract color of Fisbon is more orange-red and there is no tendency to develop a bluish cast. The difference in bract color is most visible with the primary, slightly bicolored bracts which are near 45 C in Fisbon but a more red (50A) in Peterstar. In trials to date, Fisbon has shown a somewhat more compact habit, and visible bract coloring begins about one week earlier than Peterstar.

When compare to Angelika, the parent of Peterstar and disclosed in U.S. Plant Pat. No. 5,492, Fisbon has an orange-red bract color which is more uniform and which does not tend to develop a bluish cast or to fade under less than optimum conditions. Angelika is a stronger grower, develops fertile stamens (unlike Fisbon) and has generally flat bracts.

When compared to Fispic, disclosed in a pending application, Fisbon has a less compact growth habit, orange-red bract color, and the foliage of Fisbon is a lighter green. The bracts and leaves of Fispic are narrower with longer acuminated tips and a greater degree of rugosity and lobing.

The accompanying color photographic drawing shows typical inflorescence and foliage of Fisbon, with colors being as true as possible with illustrations of this type. In the photograph, a typical mature potted plant of Fisbon appears on the left and a mature potted plant of comparison cultivar Peterstar appears on the right.

In the following description, color references are made to the Royal Horticultural Society Colour Chart. The color values were determined indoors in a north light. The plants described were grown in Hillscheid, Germany (latitude 50°N). They were planted as rooted cuttings into 14 cm pots in early August, potted in late-August and pinched 10 days later. Plants were lighted (long day conditions) from mid-September. From October 1, they grew under natural short days conditions in the greenhouse at 18° C. night temperature and 18° to 24° C. day temperature. Observations and measurements were taken at the beginning of flowering when three (3) cyathias were open.

Classification:

*Botanical.*—*Euphorbia pulcherrima.*

*Commercial.*—Poinsettia, cv. Fisbon.

Parentage: Induced mutation of Peterstar.

Plant description:

*Form.*—Broad, bushy, 9–11 branches.

*Growth habit.*—Low-medium height: 25–30 cm, compact.

*Rooting.*—Fast, less than 20 days.

*Blooming season.*—From late November (about 9 weeks of response time).

*Blooming habit.*—Saleable in late November, when 3–6 bracts are fully colored.

*Foliage.*—Size: Leaf is approximately 13–14 cm in length; petiole is 7 cm in length. Internodes: 10–15 mm. Color: New Foliage: Upper surface, medium green, between 143A and 144A; under surface 144A. Old Foliage: Upper surface, medium green 147A; under surface 137C. Leaf Petiole: Light red. Shape: Broad, elliptic with weak lobes, rounded base. Texture: Upper side, slightly rugose; lower side, weak veins. Edge of margin: Entire. Disease resistance: Neither higher tolerance nor higher susceptibility to diseases or pests have been noted.

Flowering description:

*Cyathias.*—Borne: In a narrow cluster. Quantity: 18–23. Retention: Good.

*Bracts.*—Broad elliptical; largest colored bract with petiole is 17 cm long.

*Color.*—Orange-red 42A.

*Aspect.*—Horizontal.

Reproductive organs:

*Glands, nectar cups.*—Orange-yellow.

*Stamens.*—Brown, hardly any fertile stamens.

*Pollen.*—No pollen.

*Styles.*—Red, 6-lobed stigma.

*Ovaries.*—Triangular, 3-celled, 3 ovules.

I claim:

1. A new and distinct poinsettia plant named Fisbon, as illustrated and described.

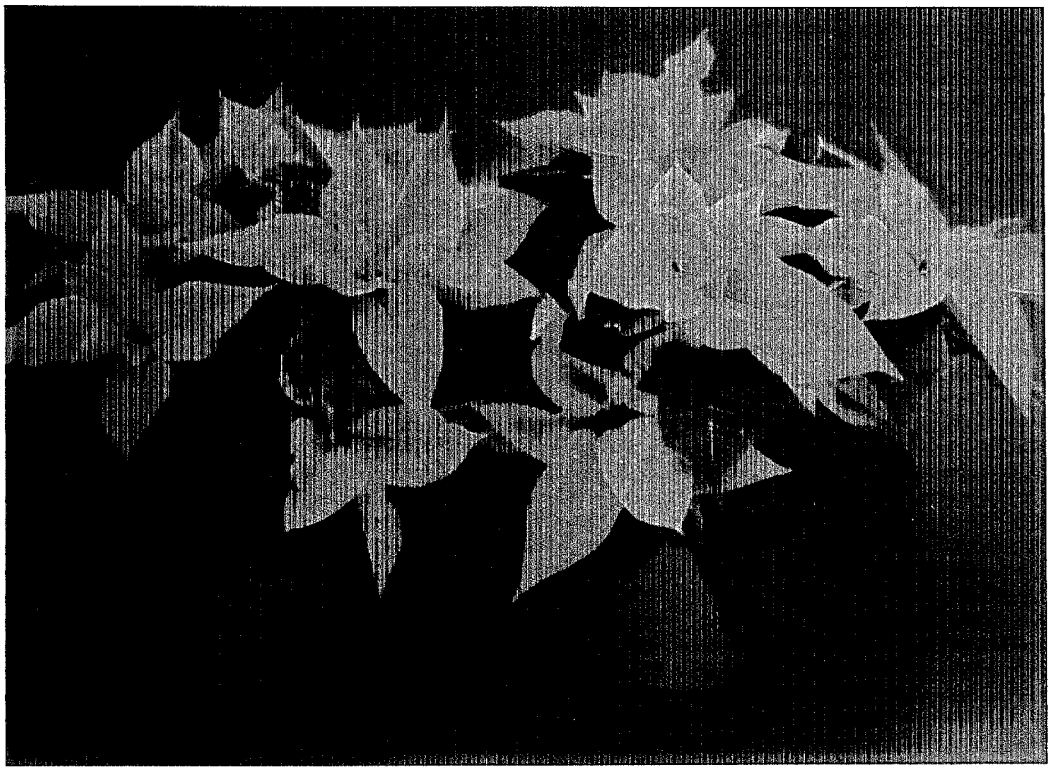

* * * * *